(12) United States Patent
Nakamura

(10) Patent No.: US 7,692,801 B2
(45) Date of Patent: Apr. 6, 2010

(54) OPTICAL STACKED STRUCTURE INSPECTING METHOD AND OPTICAL STACKED STRUCTURE INSPECTING APPARATUS

(75) Inventor: Yuki Nakamura, Tokyo (JP)

(73) Assignee: Ricoh Company, Ltd., Tokyo (JP)

( * ) Notice: Subject to any disclaimer, the term of this patent is extended or adjusted under 35 U.S.C. 154(b) by 820 days.

(21) Appl. No.: 11/415,293

(22) Filed: May 2, 2006

(65) Prior Publication Data

US 2006/0285121 A1 Dec. 21, 2006

(30) Foreign Application Priority Data

May 6, 2005 (JP) .............................. 2005-134949

(51) Int. Cl.
*G01B 11/28* (2006.01)
(52) U.S. Cl. .................... 356/630; 356/73; 356/239.3; 356/504
(58) Field of Classification Search .................. 356/73, 356/239.3, 239.7, 503, 504, 629, 630
See application file for complete search history.

(56) References Cited

U.S. PATENT DOCUMENTS

| | | | |
|---|---|---|---|
| 4,243,882 A | 1/1981 | Yasujima et al. | |
| 5,604,581 A | 2/1997 | Liu et al. | |
| 5,974,025 A | 10/1999 | Yamada et al. | |
| 6,069,703 A * | 5/2000 | Banet et al. | 356/630 |
| 6,373,802 B1 | 4/2002 | Hattori et al. | |
| 6,445,669 B1 | 9/2002 | Hattori et al. | |
| 6,744,521 B1 | 6/2004 | Hertling et al. | |
| 6,784,428 B2 * | 8/2004 | Rabolt et al. | 250/339.02 |
| 7,151,609 B2 * | 12/2006 | Chalmers et al. | 356/630 |
| 2002/0163652 A1 | 11/2002 | Mikami et al. | |
| 2004/0130726 A1 | 7/2004 | Mikkelsen et al. | |
| 2004/0257583 A1 | 12/2004 | Kim et al. | |
| 2005/0194896 A1 * | 9/2005 | Sugita et al. | 313/506 |
| 2005/0221050 A1 | 10/2005 | Shinotsuka et al. | |

FOREIGN PATENT DOCUMENTS

| | | |
|---|---|---|
| DE | 4228870 | 3/1994 |
| JP | 03-280232 | 12/1991 |
| JP | 10-122826 | 5/1998 |
| JP | 10-340483 | 12/1998 |
| JP | 11-066633 | 3/1999 |
| JP | 2000-311384 | 11/2000 |
| JP | 2001-307328 | 11/2001 |

(Continued)

OTHER PUBLICATIONS

U.S. Appl. No. 11/050,610, filed Feb. 3, 2005.

*Primary Examiner*—Gregory J Toatley, Jr.
*Assistant Examiner*—Iyabo S Alli
(74) *Attorney, Agent, or Firm*—Dickstein Shapiro LLP

(57) ABSTRACT

An inspecting method inspects an optical stacked structure having a reflection layer and at least one light transmitting thin film sequentially stacked on a substrate. The inspecting method irradiates inspection light on the optical stacked structure from a side provided with the light transmitting thin film, measures a light intensity of reflected light from each layer, that changes depending on a change in an optical path length to each layer, and inspects a thickness of the light transmitting thin film based on the light intensity of reflected light for a specific wavelength.

20 Claims, 7 Drawing Sheets

FOREIGN PATENT DOCUMENTS

| | | |
|---|---|---|
| JP | 2002-510107 | 4/2002 |
| JP | 2002-367244 | 12/2002 |
| JP | 2003-272247 | 9/2003 |
| JP | 2004-266890 | 9/2004 |
| JP | 2004-288259 | 10/2004 |
| WO | WO-99-13468 | 3/1999 |

* cited by examiner

OPTICAL STACKED STRUCTURE INSPECTING METHOD AND OPTICAL STACKED STRUCTURE INSPECTING APPARATUS

BACKGROUND OF THE INVENTION

1. Field of the Invention

The present invention generally relates to optical stacked structure inspecting methods and optical stacked structure inspecting apparatuses, and more particularly to an optical stacked structure inspecting method and an optical stacked structure inspecting apparatus for inspecting a dye layer thickness and/or a dielectric layer thickness of an optical stacked structure in which a reflection layer and an organic dye layer are successively stacked on a substrate or, a reflection layer, an organic dye layer and a dielectric layer are successively stacked on a substrate. The present invention also relates to a method and an apparatus for producing such an optical stacked structure.

2. Description of the Related Art

Generally known write-once type optical recording media, to which information can be written once by a laser beam, include CD-R, DVD+R and DVD-R. Such write-once type optical recording media have a stacked structure made up of a transparent polycarbonate substrate formed with a tracking groove, a recording layer made of an organic dye spin-coated on the substrate, a light reflection layer made of Au or Ag sputtered on the recording layer, and a projection layer made of an ultraviolet curing resin that are stacked in this order. The DVD+R and the DVD-R have a structure in which two substrates having a thickness of 0.6 mm are bonded together, and have a large recording capacity.

As a method of inspecting the layer thickness of the organic dye recording layer during the production process of the write-once type optical recording medium, a Japanese Laid-Open Patent Application No. 2002-510107 proposes a method of measuring the layer thickness based on transmitted or reflected light that is diffracted by the groove.

A Japanese Laid-Open Patent Application No. 2002-367244 proposes a method of measuring the thicknesses of a land part and a groove part based on diffracted light of different orders, and inspecting the dye layer thickness by measuring the transmittance and the diffracted light intensity in a state where the dye layer is formed on the substrate.

In addition, a Japanese Laid-Open Patent Application No. 11-66633 proposes an apparatus for inspecting defects from the reflected light using, as the inspection light, light having a characteristic absorption wavelength of the dye as a main component.

The existing DVD-ROMs for read use include those having two information recording layers for the purpose of increasing the recording capacity. A first substrate and a second substrate are bonded via a transparent intermediate layer made of an ultraviolet curing resin. A first information recording layer L0 has a semi-transparent first layer formed on an inner surface of the first substrate formed with concavo-convex pits. A second information recording layer L1 has the transparent intermediate layer and a metal reflecting second layer formed on the first information recording layer L0. The semi-transparent first layer is formed by a dielectric layer or a thin metal layer.

By converging a reproducing laser beam on the first information recording layer L0 or the second information recording layer L1 and detecting the reflected light therefrom, it is possible to reproduce the signal from the corresponding first information recording layer L0 or second information recording layer L1. Since the signals are read from the two information recording layers L0 and L1, it is possible to obtain a maximum recording capacity of approximately 8.5 GB.

Recently, a type of optical recording medium having two recording layers and having information reproducing compatibility with the DVD-ROM having the first and second information recording layers L0 and L1 has been developed. This type of optical recording medium is made up of a first substrate and a second substrate that are bonded via an adhesive agent. The first substrate includes a transparent substrate formed with a groove, a recording layer made of an organic dye formed on the substrate, a semi-transparent reflection layer formed on the recording layer, and an ultraviolet curing resin formed on the recording layer, that are stacked in this order. The second substrate includes a substrate formed with a groove, a total reflection layer formed on the substrate, a recording layer made of an organic dye formed on the substrate, and a transparent organic thin film formed on the recording layer, that are stacked in this order. Examples of this type of optical recording media are proposed in Japanese Laid-Open Patent Applications No. 10-340483 and No. 2000-311384.

However, when producing this type of optical recording medium by forming the recording layer and the semi-transparent reflection layer on each substrate and bonding the first and second substrates, there was a problem in that the thicknesses of the dye layer formed on the total reflection layer and the dielectric layer formed on the dye layer cannot be measured using the transmitted light because the light cannot be transmitted through the total reflection layer of the second substrate.

SUMMARY OF THE INVENTION

Accordingly, it is a general object of the present invention to provide a novel and useful optical stacked structure inspecting methods, optical stacked structure inspecting apparatus, optical stacked structure producing method and optical stacked structure producing apparatus, in which the problems described above are suppressed.

Another and more specific object of the present invention is to provide an optical stacked structure inspecting methods, an optical stacked structure inspecting apparatus, an optical stacked structure producing method and an optical stacked structure producing apparatus, which enable simple inspection of the thickness of each layer of the optical stacked structure having a reflection layer and at least one light transmitting thin film stacked on a substrate.

Still another object of the present invention is to provide an optical stacked structure inspecting method for inspecting an optical stacked structure having a reflection layer and at least one light transmitting thin film sequentially stacked on a substrate, the optical stacked structure inspecting method comprising (a) irradiating inspection light on the optical stacked structure from a side provided with the light transmitting thin film; (b) measuring a light intensity of reflected light from each layer, that changes depending on a change in an optical path length to each layer; and (c) inspecting a thickness of the light transmitting thin film based on the light intensity of reflected light for a specific wavelength. According to the optical stacked structure inspecting method of the present invention, it is possible to enable simple inspection of the thickness of each layer of the optical stacked structure.

A further object of the present invention is to provide an optical stacked structure inspecting apparatus for inspecting an optical stacked structure having a reflection layer and at least one light transmitting thin film sequentially stacked on a substrate, the optical stacked structure inspecting apparatus comprising a light source configured to irradiate inspection light on the optical stacked structure from a side provided with the light transmitting thin film, and an inspecting part configured to measuring a light intensity of reflected light from each layer, that changes depending on a change in an optical path length to each layer, and to inspect a thickness of the light transmitting thin film based on the light intensity of reflected light for a specific wavelength. According to the optical stacked structure inspecting apparatus of the present invention, it is possible to enable simple inspection of the thickness of each layer of the optical stacked structure.

Other objects and further features of the present invention will be apparent from the following detailed description when read in conjunction with the accompanying drawings.

DESCRIPTION OF THE PREFERRED EMBODIMENTS

Figure 1:
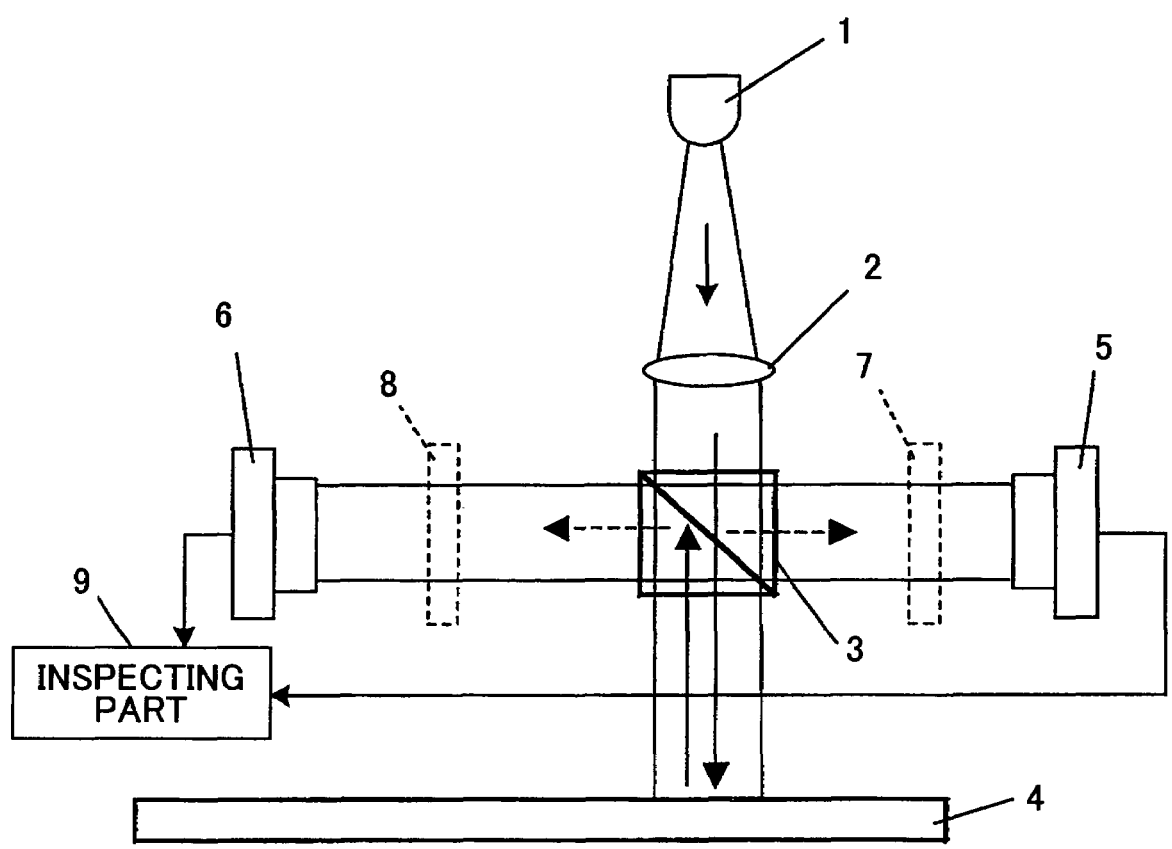
FIG. 1 is a diagram generally showing a structure of an optical stacked structure inspecting apparatus in a first embodiment of the present invention.

A description will be given of embodiments of the optical stacked structure inspecting method, the optical stacked structure inspecting apparatus, the optical stacked structure producing method and the optical stacked structure producing apparatus according to the present invention, by referring to the drawings.

FIG. 1 is a diagram generally showing a structure of the optical stacked structure inspecting apparatus in a first embodiment of the present invention, for explaining the optical stacked structure inspecting method and the optical stacked structure inspecting apparatus according to the present invention. In this embodiment, the present invention is applied to the inspection process (or checking process) for a second substrate of the write-once type optical recording medium having the recording layer with the two-layer structure when producing this write-once type optical recording medium.

In FIG. 1, a light source 1 is made of a light emitting diode and emits light in a direction indicated by an arrow. A condenser lens 2 forms the light from the light source 1 into parallel rays which pass a beam splitter 3, and light having an intensity of approximately 50% of that of the parallel rays reaches a second substrate within an optical stacked structure 4, that is, the write-once type optical recording medium having the recording layer with the two-layer structure. Remaining light split by the beam splitter 3 is monitored by an incident light photosensor 5 to measure the incident light intensity. In addition, the light reflected at the surface of the second substrate of the optical stacked structure 4 passes through the beam splitter 3 again and is received by a reflected light photosensor 6 to measure the reflected light intensity. A light separating means 7 may be provided at a stage preceding the incident light photosensor 5 with respect to the incoming light to the incident light photosensor 5 to separate a specific wavelength, and a light separating means 8 may be provided at a stage preceding the reflected light photosensor 6 with respect to the incoming light to the reflected light photosensor 6 to separate a specific wavelength. For example, the light separating means 7 may be formed by a prism or a diffraction grating.

An inspecting part 9 compares the incident light intensity measured by the incident light photosensor 5 and the reflected light intensity measured by the reflected light photosensor 6, and obtains the reflectivity of the light emitting wavelength of the light emitting diode forming the light source 1.

In this particular case, the optical stacked structure 4, that is, the write-once type optical recording medium having the recording layer with the two-layer structure, has a first substrate and the second substrate that are bonded using an adhesive agent. The first substrate has a tracking groove having a depth of 20 nm to 200 nm arranged at a pitch of 0.74 μm on a disk-shaped substrate surface. A total reflection layer made of an alloy of a metal such as Ag, Al and Au added with an element such as Cu, Pd, Pt, Zn, In, Mg, Ti, V and Ta amounting to 0.1 wt % to 3 wt % is sputtered on the substrate surface. In addition, an organic dye layer having an absorption spectrum with a maximum absorption wavelength of 580 nm to 620 nm is coated on the total reflection layer. A dye compound that can easily obtain a desired optical characteristic in the laser beam wavelength for DVD of approximately 650 nm, such as tetraazaporphyrazine dye, cyanine dye, azo dye and squarylium dye, may be used for the organic dye layer. The second substrate has a dye layer, a semi-transparent reflection layer, and a transparent dielectric layer that are stacked on the substrate surface. The transparent dielectric layer is provided to prevent elution of the dye coated on the first substrate when the first and second substrate are bonded using the adhesive agent.

In order to protect the dye from the adhesive agent, the transparent dielectric layer is desirably a compact thin layer that bonds satisfactorily with respect to the dye. Hence, the transparent dielectric layer may be made of oxides such as silicon oxide, aluminum oxide, zinc oxide and titanium oxide, nitrides such as silicon nitride and aluminum nitride, sulfides such as zinc sulfide, germanium sulfide and molybdenum sulfide, fluorides such as magnesium fluoride, cesium fluoride and barium fluoride, and suitable mixtures of such.

Next, a description will be given of the measuring principle used in the inspecting part 9 of this embodiment.

The absorbance and reflectivity of the optical stacked structure 4 were obtained by measuring the spectral reflectivity using ETA-RT manufactured by STEAG ETA-Optik.

The Ag total reflection layer had a reflectivity spectrum with a high reflectivity in a visible light region, a slightly lower reflectivity in a short wavelength region, and a higher reflectivity in a long wavelength region. When this Ag reflection layer was formed on the optical stacked structure 4 having grooves formed at equal pitches on a plastic substrate, a deterioration in the reflectivity caused by the diffraction at the grooves was observed. This deterioration in the reflectivity became greater as the depth of the grooves became deeper, and as the pitch of the grooves became smaller, the wavelengths at which the reflectivity deteriorates shifted towards the short wavelengths approximately proportionally to the pitch.

Figure 2:
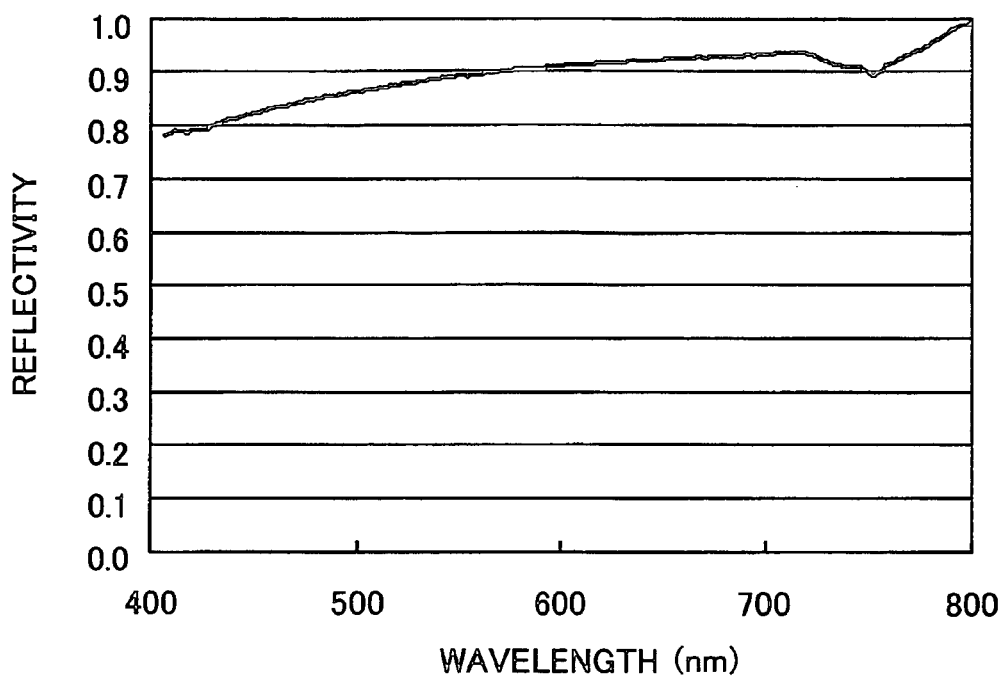
FIG. 2 is a diagram showing a relationship of the reflectivity and wavelength for a case where Ag was formed to a thickness of 140 nm on a substrate.

FIG. 2 is a diagram showing a relationship of the reflectivity and wavelength for a case where Ag was formed to a thickness of 140 nm on a polycarbonate substrate having the grooves having a depth of 33 nm and a width of 0.25 μm formed at a pitch of 0.74 μm. FIG. 2 shows the spectral reflection spectrum of the light that is perpendicularly incident to and reflects perpendicularly from the Ag total reflection layer. In this case, a phenomenon in which the reflectivity decreases by 5% to 6% due to scattering at the grooves was observed in a vicinity of the wavelength of 750 nm.

Figure 3:
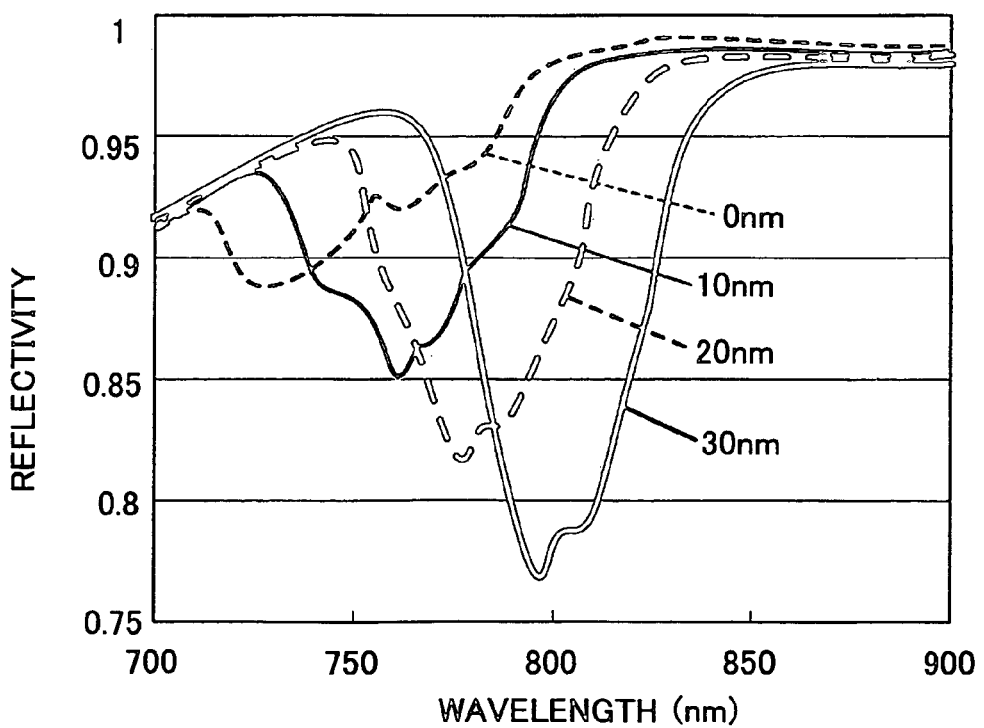
FIG. 3 is a diagram showing a relationship of the reflectivity and wavelength for a case where a dielectric layer having a composition ZnS (80 mol %)/$SiO_2$ (20 mol %) was formed to a thickness of 10 nm to 30 nm on the substrate.

FIG. 3 is a diagram showing a relationship of the reflectivity and wavelength for a case where a dielectric layer, having a composition ZnS (80 mol %)/SiO$_2$ (20 mol %), was formed to a thickness of 10 nm to 30 nm on the polycarbonate substrate formed with the Ag total reflection layer. FIG. 3 shows the spectral reflection spectrum of the light that is perpendicularly incident to and reflects perpendicularly from the surface formed with the dielectric layer. In this case, as the dielectric layer thickness increased, the wavelengths at which the minimum reflectivity is obtained shifted towards the long wavelengths in the reflectivity deteriorating portion where the wavelength is 700 nm to 850 nm, and in addition, the minimum reflectivity deteriorated.

Figure 4:
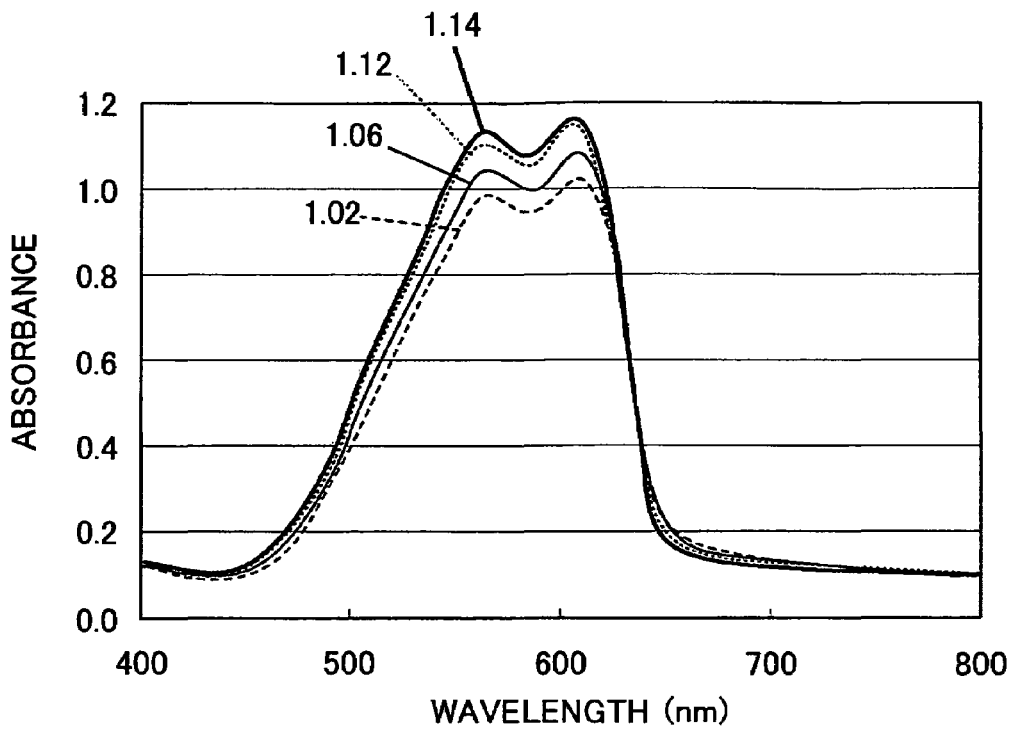
FIG. 4 is a diagram showing a relationship of the absorbance and wavelength for a case where the dye recording layer thickness was varied using a maximum absorption wavelength $\lambda$max of 606 nm as the parameter.

The recording layer was formed on the substrate formed with the Ag total reflection layer by spin-coating the squarylium dye. When the thickness of the dye recording layer was varied using a maximum absorption wavelength λmax of 606 nm as the parameter in the absorption spectrum for a case where the dye recording layer is directly coated on the substrate as in the case of producing the normal optical recording medium, a spectrum shown in FIG. 4 was obtained. FIG. 4 is a diagram showing a relationship of the absorbance and wavelength for the case where the dye recording layer thickness was varied using the maximum absorption wavelength λmax of 606 nm as the parameter so that the absorbance becomes 1.02, 1.06, 1.12 and 1.16.

Figure 5:
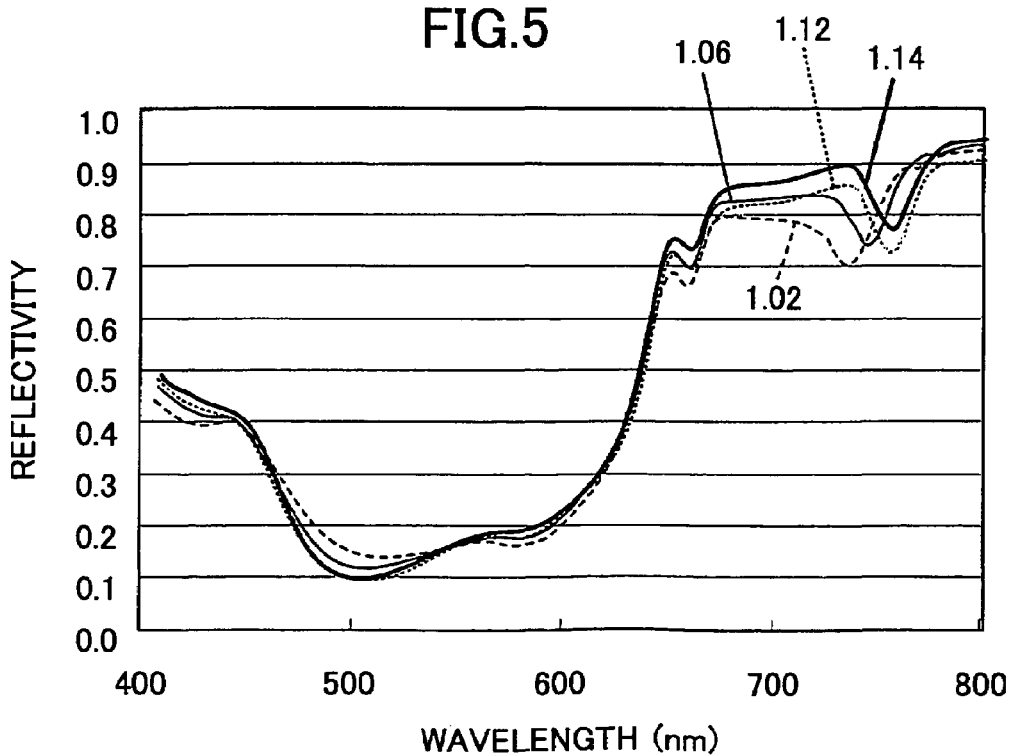
FIG. 5 is a diagram showing the relationship of the reflectivity and wavelength for a case where the dye was coated on a substrate having an Ag total reflection layer under the same condition as in FIG. 4 and annealed at 90° C. for 15 minutes.

When the dye was coated on the substrate formed with the Ag total reflection layer under the same condition as above and the reflectivity spectrum was measured after annealing at 90° C. for 15 minutes, the spectrum shown in FIG. 5 was obtained. FIG. 5 is a diagram showing the relationship of the reflectivity and wavelength for the case where the dye was coated on the substrate having the Ag total reflection layer under the same condition as in FIG. 4 and annealed at 90° C. for 15 minutes so that the absorbance becomes 1.02, 1.06, 1.12 and 1.16. As shown in FIG. 5, since the optical path length changed depending on the dye recording layer thickness, the wavelengths at which the reflectivity deteriorates shifted to the vicinity of the wavelength of 750 nm where the reflectivity deterioration was observed in FIG. 2. For this reason, it was possible to optically measure the dye recording layer thickness on the Ag total reflection layer by measuring the wavelength at which the minimum reflectivity is obtained in the range of the wavelengths of 700 nm to 800 nm or, by measuring the reflectivity at the wavelength of 740 nm.

Next, a transparent dielectric thin film was formed on the dye recording layer. When the refractive index of the transparent dielectric thin film was approximately 1.6 or less, the reflection spectrum virtually did not change before and after the transparent dielectric thin film was formed. On the other hand, when the refractive index of the transparent dielectric thin film was approximately 1.8 or greater, the reflection spectrum greatly changed before and after the transparent dielectric thin film was formed.

Figure 6:
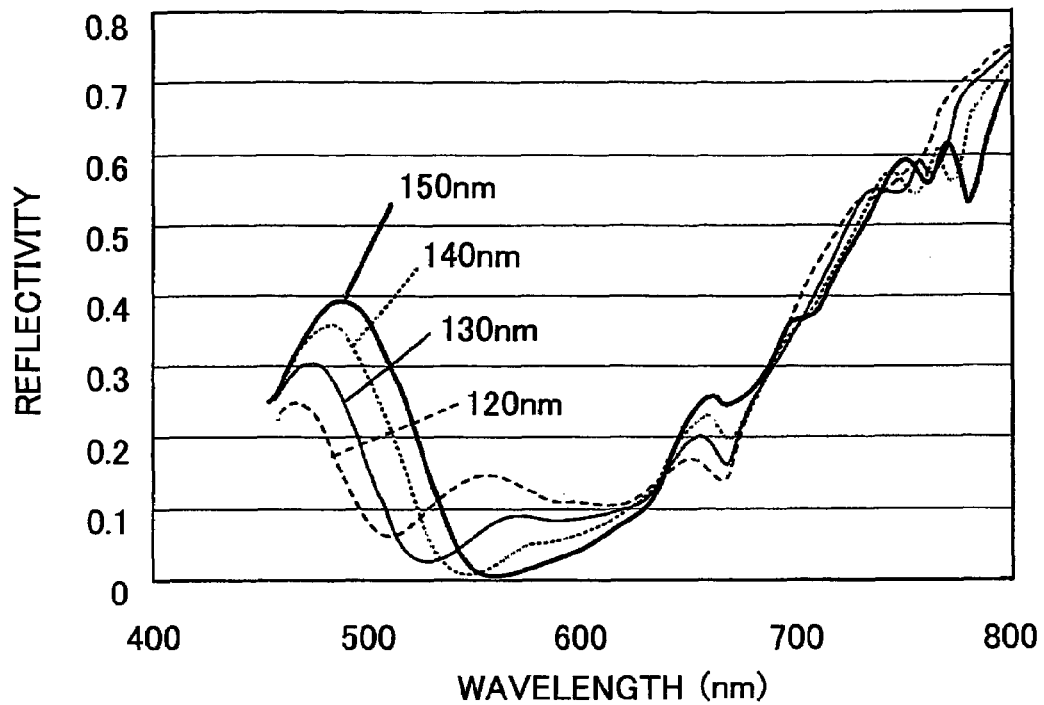
FIG. 6 is a diagram showing the relationship of the reflectivity and wavelength for a case where a transparent dielectric thin film had a refractive index of approximately 2.1 on the dye recording layer and the thickness of the transparent dielectric thin film was varied.

When another transparent dielectric thin film having a refractive index of approximately 2.1 was formed on the dye recording layer and the thickness of this transparent dielectric thin film was varied, a change was observed in the reflection spectrum as shown in FIG. 6 due to the interference between the dye recording layer and this transparent dielectric thin film. FIG. 6 is a diagram showing the relationship of the reflectivity and wavelength for a case where the transparent dielectric thin film had the refractive index of approximately 2.1 on the dye recording layer and the thickness of the transparent dielectric thin film was varied. As may be seen from FIG. 6, it was possible to optically measure the thickness of the transparent dielectric thin film on the dye recording layer by measuring the reflectivity peak wavelength or the reflectivity in the vicinity of the wavelength of 490 nm or 660 nm.

The methods of measuring the thicknesses of the dye recording layer and the transparent dielectric thin film of the optical stacked structure using the reflection spectrum are not limited to the measurements of the dye material and the dielectric material and are similarly applicable to materials in general, by appropriately selecting the optimum wavelength depending on the target material with respect to which the measurement is to be made.

Figure 7:
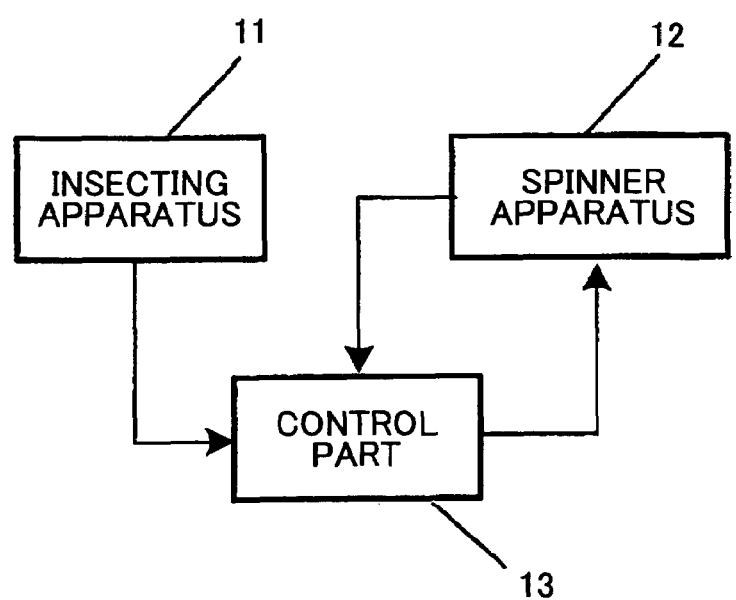
FIG. 7 is a diagram showing a control system of the first embodiment of the present invention in a simplified manner.

The results of the measurements obtained by the methods described above and an inspecting apparatus 11 after coating the dye may be fed back via a control part 13 to a spinner apparatus 12 shown in FIG. 7 which forms the optical stacked structure producing apparatus. FIG. 7 is a diagram showing a control system of the first embodiment of the present invention in a simplified manner. In this case, the control part 13 is formed by a CPU or the like for adjusting the overshoot rotational speed or overshoot time. Bu using the optical stacked structure having the feedback structure shown in FIG. 7, it is possible to obtain a dye recording layer having an extremely small variation in the dye recording layer thickness.

The results of the measurements obtained after sputtering the transparent dielectric thin film may be fed back to a sputtering apparatus (not shown) which forms the optical stacked structure producing apparatus. In this case, it is possible to obtain a dye recording layer and a transparent dielectric thin film having an extremely small variation in the dye recording layer thickness and the transparent dielectric thin film thickness. Hence, by using such dye recording layer and transparent dielectric thin film, it is possible to produce an optical recording medium having an extremely stable quality before and after the information recording.

In this embodiment, it is possible to utilize the wavelengths mainly including the visible light wavelength such as that from a lamp.

Figure 8:
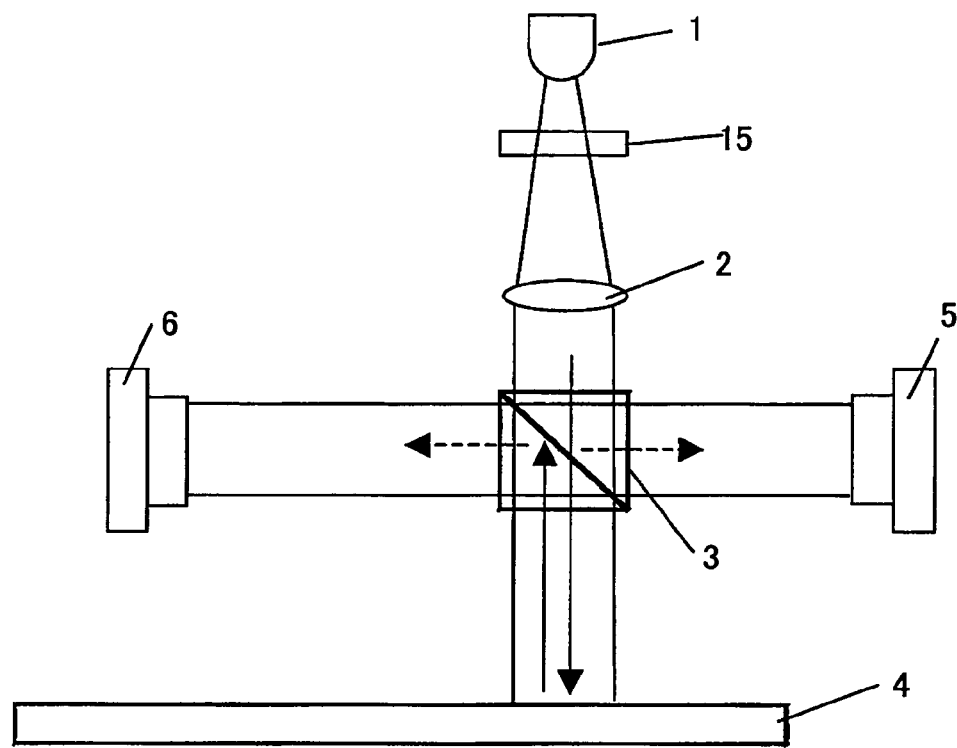
FIG. 8 is a diagram generally showing a structure of the optical stacked structure inspecting apparatus in a second embodiment of the present invention.

FIG. 8 is a diagram generally showing a structure of the optical stacked structure inspecting apparatus in a second embodiment of the present invention. In FIG. 8, those parts that are the same as those corresponding parts in FIG. 1 are designated by the same reference numerals, and a description thereof will be omitted. In this case, the measuring wavelengths and bandwidths are already determined. Hence, it is possible to considerably reduce the cost of the apparatus by using a bandpass filter 15 for passing a desired wavelength and using a light emitting diode as the light source 1.

Figure 9:
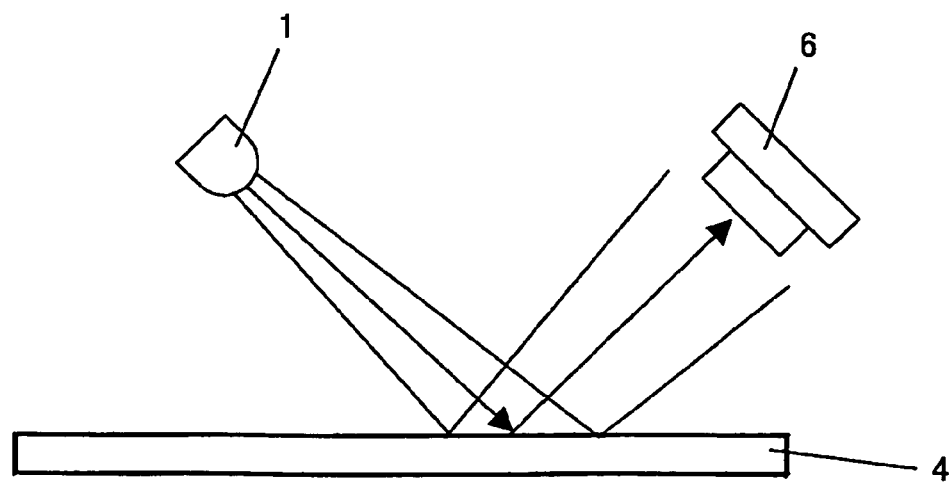
FIG. 9 is a diagram generally showing a structure of the optical stacked structure inspecting apparatus in a third embodiment of the present invention.

FIG. 9 is a diagram generally showing a structure of the optical stacked structure inspecting apparatus in a third embodiment of the present invention. In FIG. 9, those parts that are the same as those corresponding parts in FIG. 1 are designated by the same reference numerals, and a description thereof will be omitted. In this case, an inspection similar to that described above is made using a diffusing optical system and the light source 1 such as a light emitting diode that irradiates light obliquely with respect to the substrate surface of the optical stacked structure 4.

Therefore, the optical stacked structure inspecting method and the optical stacked structure inspecting apparatus for inspecting the optical stacked structure having the reflection layer and at least one light transmitting thin film sequentially stacked on the substrate, irradiate the inspection light on the optical stacked structure from a side provided with the light transmitting thin film, measure the light intensity of reflected light from each layer, that changes depending on the change in the optical path length to each layer, and inspect a thickness of the light transmitting thin film based on the light intensity of reflected light for a specific wavelength. Accordingly, it is possible to inspect the thickness of each layer of the optical stacked structure with a high accuracy. In addition, by controlling the thickness of each layer based on the measured thickness during the production of the optical stacked structure, it is possible to produce an optical stacked structure having a high quality.

Next, a description will be given of embodiment samples of the present invention.

First Embodiment Sample

A concavo-convex pattern of guide grooves having a depth of approximately 30 nm and a groove width of approximately 0.25 μm were formed with a track pitch of 0.74 μm on a polycarbonate substrate having a diameter of 120 mm and a thickness of 0.60 mm. a material having a composition Ag (98 wt %)/Cu (2 wt %) was sputtered to a thickness of approximately 140 nm by a sputtering apparatus (model name Big Sprinter) manufactured by Unaxis using Ar as a sputtering gas at a sputtering pressure of $6.0 \times 10^{-3}$ Torr and a D.C. sputtering power of 3.5 kW, so as to form the reflection layer. Next, a squarylium dye compound was spin-coated on the reflection layer to a layer thickness such that the absorbance at the maximum absorption wavelength λmax becomes 1.02, 1.06, 1.12 and 1.16.

Figure 10:
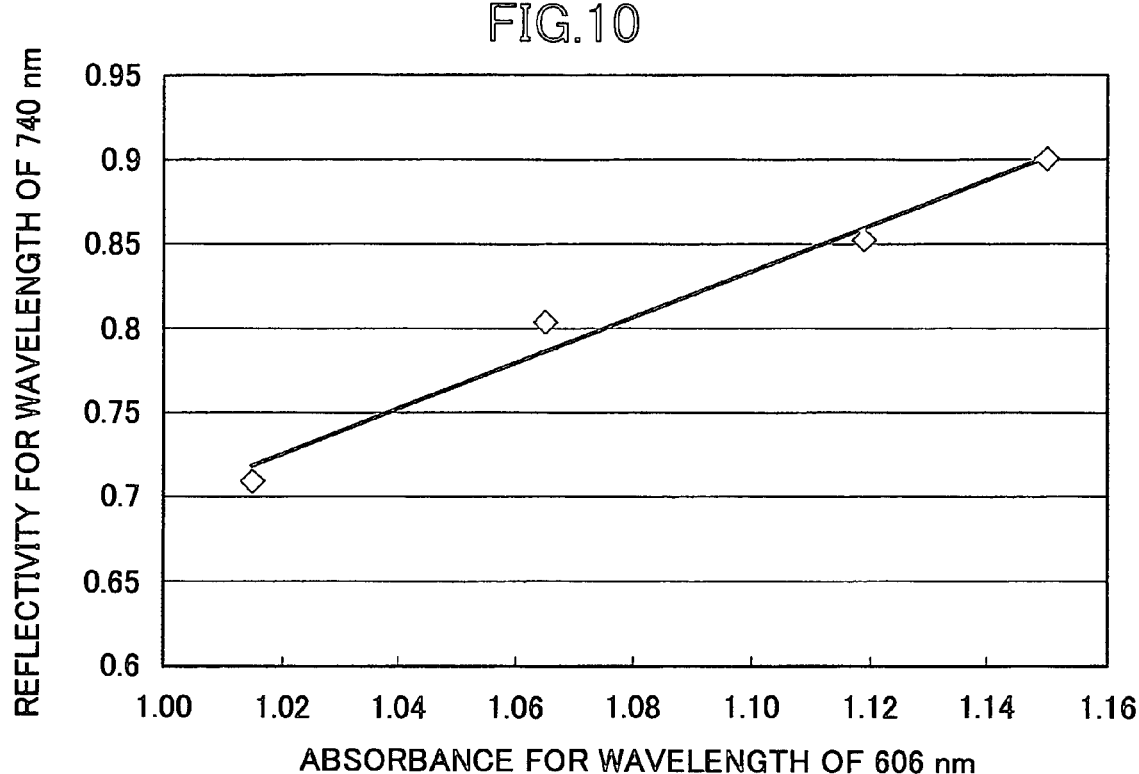
FIG. 10 is a diagram showing the relationship of the reflectivity for a wavelength of 740 nm and the absorbance for a wavelength of 606 nm.

Thereafter, the dye surface reflectivity of the substrate structure of this first embodiment sample was measured by ETA-RT at the wavelength of 740 nm. The results shown in FIG. 10 were obtained by this measurement. FIG. 10 is a diagram showing the relationship of the reflectivity for the wavelength of 740 nm and the absorbance for the wavelength of 606 nm, and it may be seen that there is an extremely strong correlation between the two.

Second Embodiment Sample

A material having a composition ZnS (80 mol %)/SiO$_2$ (20 mol %) was sputtered to thicknesses of 120 nm, 130 nm, 140 nm and 150 nm on the substrate structure of the first embodiment sample described above by the sputtering apparatus (model name Big Sprinter) manufactured by Unaxis using Ar as the sputtering gas at the sputtering pressure of $4.0 \times 10^{-3}$ Torr and an RF sputtering power of 4.0 kW, so as to form the dielectric layer.

Figure 11:
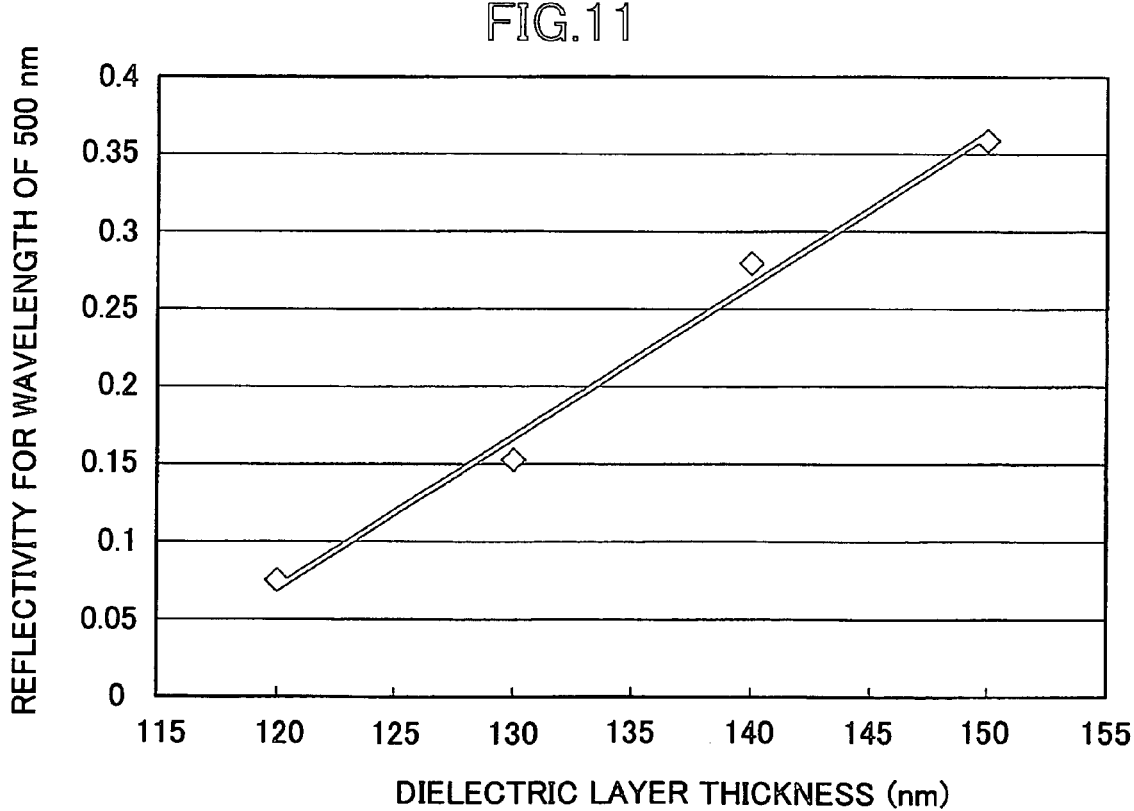
FIG. 11 is a diagram showing the relationship of the reflectivity for a wavelength of 500 nm and the dielectric layer thickness.

Then, the dielectric surface reflectivity of the substrate structure of this second embodiment sample was measured similarly by the ETA-RT at the wavelength of 500 nm. The results shown in FIG. 11 were obtained by this measurement. FIG. 11 is a diagram showing the relationship of the reflectivity for the wavelength of 500 nm and the dielectric layer thickness, and it may be seen that there is an extremely strong correlation between the two.

Third Embodiment Sample

A concavo-convex pattern of guide grooves having a depth of approximately 30 nm and a groove width of approximately 0.25 μm were formed with a track pitch of 0.74 μm on a polycarbonate substrate having a diameter of 120 mm and a thickness of 0.60 mm. A material having a composition Ag (98 wt %)/Cu (2 wt %) was sputtered to a thickness of approximately 120 nm by the sputtering apparatus (model name Big Sprinter) manufactured by Unaxis using Ar as the sputtering gas at the sputtering pressure of $6.0 \times 10^{-3}$ Torr and the D.C. sputtering power of 3.5 kW, so as to form the reflection layer. Next, a material having a composition ZnS (80 mol %)/SiO$_2$ (20 mol %) was sputtered to thicknesses of 10 nm, 20 nm and 30 nm on the substrate structure by the sputtering apparatus (model name Big Sprinter) manufactured by Unaxis using Ar as the sputtering gas at the sputtering pressure of $4.0 \times 10^{-3}$ Torr and the RF sputtering power of 4.0 kW, so as to form the dielectric layer.

Figure 12:
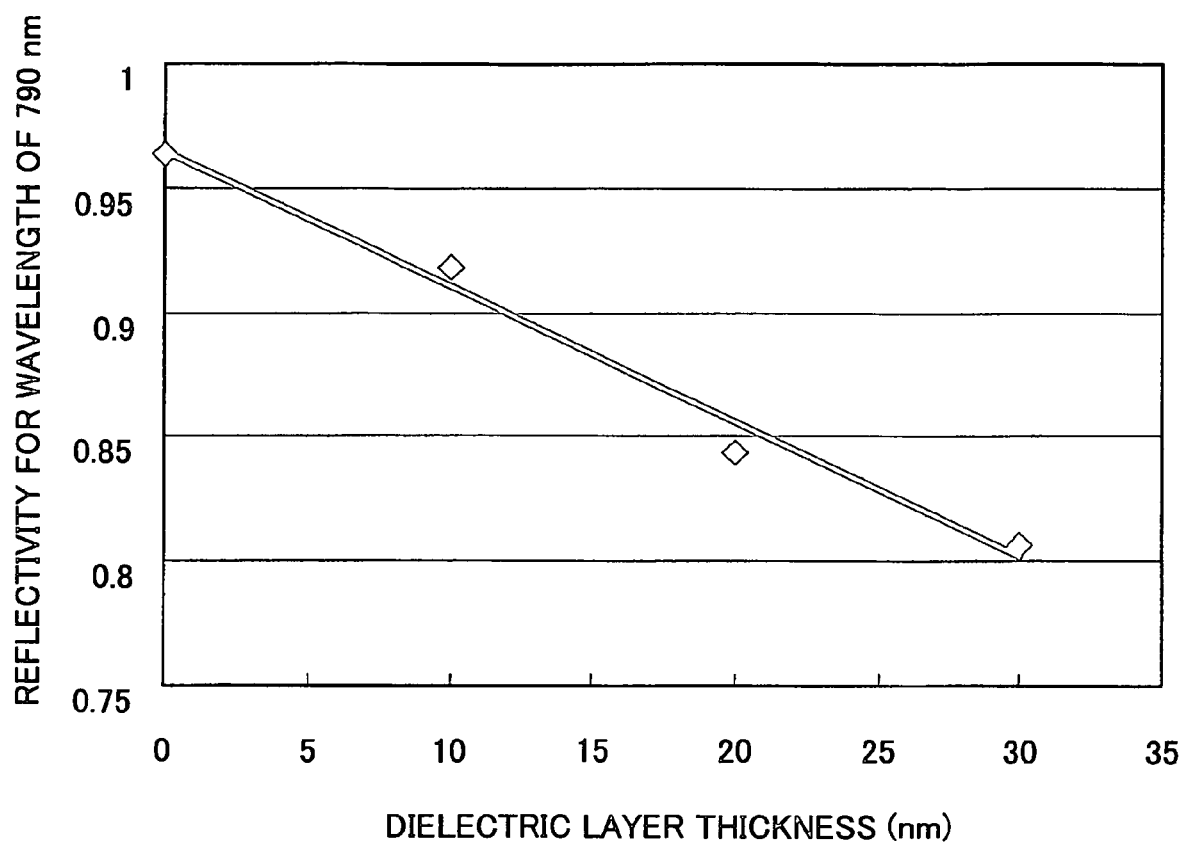
FIG. 12 is a diagram showing the relationship of the reflectivity for a wavelength of 790 nm and the dielectric layer thickness.

Then, the dielectric surface reflectivity of the substrate structure of this third embodiment sample was measured similarly by the ETA-RT at the wavelength of 790 nm. The results shown in FIG. 12 were obtained by this measurement. FIG. 12 is a diagram showing the relationship of the reflectivity for the wavelength of 790 nm and the dielectric layer thickness, and it may be seen that there is an extremely strong correlation between the two.

Therefore, the present invention is applicable to the inspection of the layer thickness of the dye layer and/or the dielectric layer of the write-once type optical recording medium having the recording layer with the two-layer structure, such as the CD-R/RW, DVD-ROM, DVD+R/RW, DVD+R/RW, DVD-R/RW and DVD-RAM, in which the optical stacked structure has the reflection layer and the organic dye layer sequentially stacked on the substrate or, the optical stacked structure in which the reflection layer, the organic dye layer and the dielectric layer are sequentially stacked on the substrate.

In addition, although the present invention is applied to the inspection of the optical stacked structure having the organic dye layer in the embodiments described above, the optical stacked structure may have any organic layer, such as ion compounds, as long as the absorption spectrum is obtainable.

This application claims the benefit of a Japanese Patent Application No. 2005-134949 filed May 6, 2005, in the Japanese Patent Office, the disclosure of which is hereby incorporated by reference.

Further, the present invention is not limited to these embodiments, but various variations and modifications may be made without departing from the scope of the present invention.

What is claimed is:

1. An optical stacked structure inspecting method for inspecting an optical stacked structure having a reflection layer and at least one light transmitting thin film sequentially stacked on a substrate, said optical stacked structure inspecting method comprising:
   (a) irradiating inspection light on the optical stacked structure from a side provided with the light transmitting thin film;
   (b) measuring a light intensity of reflected light from each layer, that changes depending on a change in an optical path length to each layer; and
   (c) inspecting a thickness of the light transmitting thin film based on the light intensity of reflected light for a specific wavelength.

2. The optical stacked structure inspecting method as claimed in claim 1, wherein:
   the substrate of the optical stacked structure has guide grooves formed thereon, and the reflection layer and an organic material layer are sequentially stacked on the substrate;
   said step (b) measures the light intensity of the reflected light from the organic material layer; and
   said step (c) inspects the thickness of the organic material layer.

3. The optical stacked structure inspecting method as claimed in claim 1, wherein:
   the substrate of the optical stacked structure has guide grooves formed thereon, and the reflection layer and a dielectric layer are sequentially stacked on the substrate;
   said step (b) measures the light intensity of the reflected light from the dielectric layer; and
   said step (c) inspects the thickness of the dielectric layer.

4. The optical stacked structure inspecting method as claimed in claim 1, wherein:
   the substrate of the optical stacked structure has guide grooves formed thereon, and the reflection layer, an organic material layer and a dielectric layer are sequentially stacked on the substrate;
   said step (b) measures the light intensity of the reflected light from the dielectric layer; and
   said step (c) inspects the thickness of the dielectric layer.

5. The optical stacked structure inspecting method as claimed in claim 1, wherein:
   the substrate of the optical stacked structure has guide grooves formed thereon, and the reflection layer, a dielectric layer and an organic material layer are sequentially stacked on the substrate;
   said step (b) measures the light intensity of the reflected light from the organic material layer; and
   said step (c) inspects the thickness of the organic material layer.

6. The optical stacked structure inspecting method as claimed in claim 1, wherein:
   the substrate of the optical stacked structure has guide grooves formed thereon, and the reflection layer, a first dielectric layer, an organic material layer and a second dielectric layer are sequentially stacked on the substrate;
   said step (b) measures the light intensity of the reflected light from the second dielectric layer; and
   said step (c) inspects the thickness of the second dielectric layer.

7. The optical stacked structure inspecting method as claimed in claim 1, wherein said step (a) uses a light emitting diode to emit the inspecting light having the specific wavelength.

8. The optical stacked structure inspecting method as claimed in claim 1, wherein said step (b) measures the light intensity of the reflected light reflected by the optical stacked structure and having the specific wavelength that is separated by light separating means.

9. The optical stacked structure inspecting method as claimed in claim 8, wherein a prism is used as the light separating means.

10. The optical stacked structure inspecting method as claimed in claim 8, wherein a diffraction grating is used as the light separating means.

11. An optical stacked structure inspecting apparatus for inspecting an optical stacked structure having a reflection layer and at least one light transmitting thin film sequentially stacked on a substrate, said optical stacked structure inspecting apparatus comprising:
    a light source configured to irradiate inspection light on the optical stacked structure from a side provided with the light transmitting thin film; and
    an inspecting part configured to measure a light intensity of reflected light and a spectral reflection spectrum of the light that is perpendicularly incident to and reflects perpendicularly from each layer, that changes depending on a change in an optical path length to each layer, and to inspect a thickness of the light transmitting thin film based on the measured light intensity of reflected light and the measured spectral reflection spectrum.

12. The optical stacked structure inspecting apparatus as claimed in claim 11, wherein:
    the substrate of the optical stacked structure has guide grooves formed thereon, and the reflection layer and an organic material layer are sequentially stacked on the substrate; and
    said inspecting part measures the light intensity of the reflected light and the spectral reflection spectrum from the organic material layer, and inspects the thickness of the organic material layer.

13. The optical stacked structure inspecting apparatus as claimed in claim 11, wherein:
    the substrate of the optical stacked structure has guide grooves formed thereon, and the reflection layer and a dielectric layer are sequentially stacked on the substrate; and
    said inspecting part measures the light intensity of the reflected light and the spectral reflection spectrum from the dielectric layer, and inspects the thickness of the dielectric layer.

14. The optical stacked structure inspecting apparatus as claimed in claim 11, wherein:
    the substrate of the optical stacked structure has guide grooves formed thereon, and the reflection layer, an organic material layer and a dielectric layer are sequentially stacked on the substrate; and
    said inspecting part measures the light intensity of the reflected light and the spectral reflection spectrum from the dielectric layer, and inspects the thickness of the dielectric layer.

15. The optical stacked structure inspecting apparatus as claimed in claim 11, wherein:

the substrate of the optical stacked structure has guide grooves formed thereon, and the reflection layer, a dielectric layer and an organic material layer are sequentially stacked on the substrate; and said inspecting part measures the light intensity of the reflected light and the spectral reflection spectrum from the organic material layer, and inspects the thickness of the organic material layer.

16. The optical stacked structure inspecting apparatus as claimed in claim 11, wherein:

the substrate of the optical stacked structure has guide grooves formed thereon, and the reflection layer, a first dielectric layer, an organic material layer and a second dielectric layer are sequentially stacked on the substrate; and said inspecting part measures the light intensity of the reflected light and the spectral reflection spectrum from the second dielectric layer, and inspects the thickness of the second dielectric layer.

17. The optical stacked structure inspecting apparatus as claimed in claim 11, wherein said light source includes a light emitting diode configured to emit the inspecting light having the specific wavelength.

18. The optical stacked structure inspecting apparatus as claimed in claim 11, wherein said inspecting part measures the light intensity of the reflected light and the spectral reflection spectrum reflected by the optical stacked structure and having the specific wavelength that is separated by light separating means.

19. The optical stacked structure inspecting apparatus as claimed in claim 18, wherein said light separating means includes a prism.

20. The optical stacked structure inspecting apparatus as claimed in claim 18, wherein said light separating means includes a diffraction grating.

* * * * *